United States Patent [19]
Jeannin

[11] Patent Number: 6,001,384
[45] Date of Patent: Dec. 14, 1999

[54] METHOD FOR FIGHTING AGAINST MYIASIS AFFECTING CATTLE AND SHEEP POPULATIONS AND COMPOSITIONS FOR IMPLEMENTING SAME

[75] Inventor: Philippe Jeannin, Tournefeuille, France

[73] Assignee: Merial, Lyon, France

[21] Appl. No.: 09/051,693

[22] PCT Filed: Aug. 19, 1997

[86] PCT No.: PCT/FR97/01504

§ 371 Date: Jul. 27, 1998

§ 102(e) Date: Jul. 27, 1998

[87] PCT Pub. No.: WO98/07423

PCT Pub. Date: Feb. 26, 1998

[30] Foreign Application Priority Data

Aug. 20, 1996 [FR] France ................... 96 10312

[51] Int. Cl.$^6$ ............ A01N 25/02; A01N 43/56
[52] U.S. Cl. ............ 424/405; 424/407; 424/408; 424/409; 424/438; 424/442; 424/450; 424/451; 424/456; 424/464; 424/484; 424/489; 424/490; 424/45; 424/46; 424/47; 424/DIG. 8; 514/407; 514/937; 514/944; 514/962
[58] Field of Search ................... 514/407, 937, 514/944, 945, 947, 962, 963, 969; 424/45–47, 405–410, 438, 442, 450, 451, 456, 464, 484, 489, 490, 499

[56] References Cited

U.S. PATENT DOCUMENTS 4,963,575  10/1990  Buntain et al. ................... 514/359

OTHER PUBLICATIONS

Siegmund et al. Ed.—Merck Veterinary Brent Manual pp. 740–746, Merck, 1973.

Primary Examiner—Neil S. Levy
Attorney, Agent, or Firm—Frommer Lawrence & Haug LLP; William S. Frommer; Thomas J. Kowalski

[57] ABSTRACT

Process for controlling myiasis in cattle and sheep livestock and compositions for carrying out this process.

Composition for topical or parenteral use for controlling myiasis in cattle and sheep, with an effective larvicidal amount of a compound of formula I, in particular Fipronil.

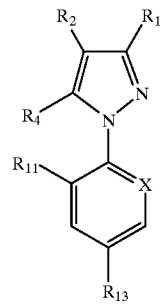

(I)

53 Claims, No Drawings

METHOD FOR FIGHTING AGAINST MYIASIS AFFECTING CATTLE AND SHEEP POPULATIONS AND COMPOSITIONS FOR IMPLEMENTING SAME

The present invention relates to an improvement to processes for controlling myiasis in large animals such as cattle and sheep. The invention also relates to compositions for carrying out this process, and to the use of known parasiticides for the preparation of such compositions.

Myiasis, which is an extremely widespread parasitosis, originates from various species of flies which lay their eggs on the animal, generally in a wound, after which the larvae resulting from hatching of the eggs grow in the subcutaneous or muscle tissues and result in deep wounds which become overinfected, often requiring the slaughter of the infested animal.

Cattle and sheep, in particular those which are reared in open pasture, in which the parasite density may be extreme, depending on the region, are subject to many wounds which serve as a point of entry. Moreover, the parasites which cause myiasis tend to attack the animals systematically after operations such as castration, removal of the horns and branding, thereby making it necessary to carry out difficult and expensive monitoring of these animals, without preventing considerable losses.

Direct control of the adult flies by treating the animal is practically inconceivable since these insects generally spend very little time on the animal. Controlling the larval stages is also much more difficult than controlling the usual ectoparasites or external parasites.

Certain systemic-action organophosphorus compounds may be used with relative success, but these compounds are generally relatively active only on certain species of flies, which complicates the control of these parasites.

Certain endectocidal compounds with systemic action, in particular ivermectin, are effective but expensive.

In the case of established myiasis, treatment with certain insecticides, in particular organophosphorus agents, allows the larvae to be destroyed. However, the cicatrization of deep wounds takes a long time, during which time the animal's wound tends to become reinfested, thereby necessitating monitoring and further treatments of the animal.

The invention proposes to overcome these drawbacks and to provide an improved process for controlling myiasis which is simple, inexpensive, highly effective over a very long period and entirely compatible with the constraints of open-pasture rearing, including that in regions which are subject to very high parasite densities.

Another aim of the invention is to provide an improved, inexpensive process for preventing myiasis under conditions of open-pasture rearing.

Another aim of the invention is to provide a process for controlling myiasis which allows the affected animal to be treated, including that in the case of large wounds, and to ensure, in a single step, elimination of the myiasis and cicatrization of the wound sufficiently to prevent the wound from being reinfested by flies, all this being without the need for any specific surveillance or a further operation on the animal.

A new family of insecticides based on 1-N-phenylpyrazoles has been described in patents EP-A-295,217 and EP-A-352,944. These compounds, which are extremely active against a certain number of plant parasites, as well as against animal parasites such as fleas, have not been described in applications for the prevention or treatment of myiasis, although the case of the flies which cause myiasis has been mentioned.

In point of fact, an extremely effective means of control for the prevention and treatment of myiasis poses many, sometimes contradictory, requirements which are extremely difficult to satisfy simultaneously.

Thus, the active compound should be inexpensive and easy to administer to the animal. It should have a persistent action, thus avoiding the addition of many treatment steps. It should also effectively prevent or eliminate other parasites liable to create points of entry for the flies which give rise to myiasis.

The subject of the invention is a process for controlling myiasis in cattle and sheep livestock, characterized in that a larvicidal dose of a compound of formula I

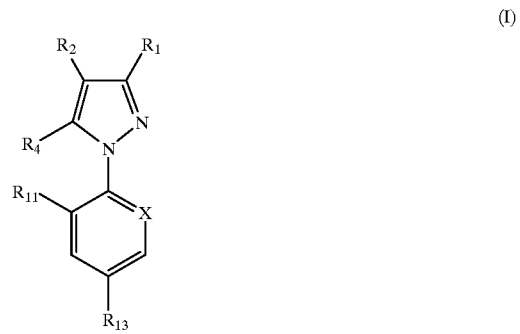

in which:

$R_1$ is a halogen atom, CN or methyl;

$R_2$ is $S(O)_n R_3$ or haloalkyl;

$R_3$ is alkyl or haloalkyl;

$R_4$ represents a hydrogen or halogen atom; or a radical $NR_5 R_6$, $S(O)_m R_7$, $C(O)R_7$ or $C(O)OR_7$, alkyl, haloalkyl or $OR_8$ or a radical $N=C(R_9)(R_{10})$;

$R_5$ and $R_6$ independently represent a hydrogen atom or an alkyl, haloalkyl, C(O)alkyl or $S(O)_r CF_3$ radical; where $R_5$ and $R_6$ may together form a divalent alkylene radical which may be interrupted with one or two divalent hetero atoms, such as oxygen or sulphur;

$R_7$ represents an alkyl or haloalkyl radical;

$R_8$ represents an alkyl or haloalkyl radical or a hydrogen atom;

$R_9$ represents an alkyl radical or a hydrogen atom;

$R_{10}$ represents a phenyl or heteroaryl group optionally substituted with one or more halogen atoms or groups such as OH, —O-alkyl, —S-alkyl, cyano or alkyl;

$R_{11}$ and $R_{12}$ represent, independently of each other, a hydrogen or halogen atom and optionally CN or $NO_2$, but H or halogen being preferred;

$R_{13}$ represents a halogen atom or a haloalkyl, haloalkoxy, $S(O)_q CF_3$ or $SF_5$ group;

m, n, q and r represent, independently of each other, an integer equal to 0, 1 or 2;

X represents a trivalent nitrogen atom or a radical $C-R_{12}$, the other three valencies of the carbon atom forming part of the aromatic ring;

with the proviso that, when $R_1$ is methyl, then $R_3$ is haloalkyl, $R_4$ is $NH_2$, $R_{11}$ is Cl, $R_{13}$ is $CF_3$ and X is N, is administered to the animal.

The alkyl radicals in the definition of formula (I) generally comprise from 1 to 6 carbon atoms. The ring formed by the divalent alkylene radical representing $R_5$ and $R_6$ as well as the nitrogen atom to which $R_5$ and $R_6$ are attached is generally a 5-, 6- or 7-membered ring.

A preferred class of compounds of formula (I) comprises compounds such that $R_1$ is CN, and/or $R_3$ is haloalkyl, and/or $R_4$ is $NH_2$, and/or $R_{11}$ and $R_{12}$ are, independently of each other, a halogen atom, and/or $R_{13}$ is haloalkyl.

A compound of formula (I) which is most particularly preferred in the invention is 1-[2,6-$Cl_2$ 4-$CF_3$phenyl]3-CN4-[SO—$CF_3$]5-$NH_2$pyrazole, referred to hereinbelow as compound A and whose common name is Fipronil.

Compounds of Formula (I) may be prepared according to one or other of the processes described in patent applications WO 87/3781, 93/6089, 94/21606 or European patent application 295,117, or any other process falling within the competence of a specialist skilled in the art of chemical synthesis. For the chemical preparation of the products of the invention, a person skilled in the art is considered as having at his or her disposal, inter alia, all of the contents of "Chemical Abstracts" and the documents which are cited therein.

The subject of the invention is, in particular, such a process of prevention or such a process of treatment of cattle against Oestridae, and in particular Dermatobia hominis, that is to say "berne", and possibly Hypoderma bovis and Hypoderma lineatum (cattle grubs), as well as against Calliphoridae, and in particular Cochliomyia hominivorax or Macellaria (screw worm).

The process according to the invention is also, however, and, if necessary, simultaneously effective against other myiases in cattle.

More particularly, the process according to the invention applies also to sheep, to control Calliphoridae, and in particular Luciliae (blow flies), especially *Lucilia cuprina* and *Lucilia sericata*, as well as to control Oestridae, and in particular *Oestrus ovis*.

In accordance with an advantageous characteristic of the invention, the administration to the animal under conditions of open-pasture rearing takes place only once in the season or a small number of times and particularly, preferably, not more than four times, at spaced-out intervals. In other words, the frequency of administration is annual or at most equal to a monthly frequency during the myiasis season and, preferably, equal to a frequency very much lower than a monthly frequency, in a variant of the process which allows the prevention of myiasis, including its prevention in regions subject to a very high parasite density.

Similarly, a process for treating myiasis which is already established, including that in the case of large wounds, is advantageously characterized by a single administration of the above said compound.

Preferably, the treatment is performed by administration of the compound in the form of a solution, suspension or emulsion to be poured onto the animal's back ("pour-on" type solution) and it is remarkable to note that this treatment is extremely effective in both animals reared in open pasture and castrated animals.

In the case of treatments according to the invention of very long duration, an administration of the controlled-release type may, however, be preferred, for example in oral form, especially intraruminal bolus, or in parenteral form, especially nanoparticles or nanospheres or microparticles, in particular microspheres or microbeads, or even implants.

However, for the local treatment of a wound infested with the larvae which cause myiasis, it is preferred to administer the compound according to the invention directly onto the surface of the wound, in the form of a spray, a solid or liquid aerosol or an emulsion, cream or paste to be spread on.

It is remarkable to note that, on animals reared in open pasture, the process according to the invention ensures not only the destruction of the larvae liable to cause myiasis, but also reduces the frequency of the possible points of entry for the laying fly, by virtue of its high efficacy against the ectoparasites liable to cause such wounds, and in particular ticks.

The efficacy of the treatment advantageously makes it possible to stop all application from 1 to 3 months before slaughter.

The subject of the invention is also compositions for carrying out this process, these compositions containing the above said compound of formula I defined above in an effective larvicidal amount in a vehicle which is suitable for administration to the animal. Preferably, in particular for prevention, the composition may be formulated to allow a systemic distribution of the said compound.

For a composition intended for administration onto the skin, the dose delivered by applying the composition is advantageously between 0.01 and 100 mg/kg and more preferably between 0.1 and 10 mg/kg.

For Fipronil, the preferred dose is between 0.25 and 2.5 mg/kg, for example 1 mg/kg.

Preferably, a composition for administration to the skin is prepared in the form of a solution, suspension or emulsion to be poured onto the animal's back, this also being referred to as a "pour-on" composition. Such solutions may be applied onto the animal's back, for example, using a measured-dose bottle or a measured-dose spray gun.

The abovementioned dose, for the animal, is advantageously contained in a vehicle whose volume is between 5 ml and 150 ml for cattle. The solution for application to the skin may be administered in particular at a rate of 5 to 20 ml per 100 kg, preferably about 10 ml per 100 kg, with a total volume of 10 to 50 ml per animal. In sheep, the dose is preferably contained in a volume to be poured on of between 10 ml and 5 l depending on the thickness of the fleece.

In such pour-on compositions, the concentration of compounds of formula I by weight per unit volume is preferably between 0.1 and 10%.

The concentration may thus be from 0.05 to 25% weight/volume.

These solutions for application to the skin generally comprise a diluent or vehicle and also a solvent (organic solvent) for the compound of formula (I) if it is not soluble in the diluent.

As organic solvents which may be used in the invention, mention may be made, in particular, of: acetyl tributyl citrate, fatty acid esters such as the dimethyl ester, diisobutyl adipate, acetone, acetonitrile, benzyl alcohol, butyl diglycol, dimethylacetamide, dimethylformamide, dipropylene glycol n-butyl ether, ethanol, isopropanol, methanol, ethylene glycol monoethyl ether, monomethylacetamide, dipropylene glycol monoethyl ether, liquid polyoxyethylene glycols, propylene glycol, 2-pyrrolidone, in particular N-methylpyrrolidone, diethylene glycol monoethyl ether, ethylene glycol, diethyl phthalate or a mixture of at least two of these.

As vehicle or diluent, mention may be made in particular of:

plant oils such as soybean oil, groundnut oil, castor oil, corn oil, cottonseed oil, olive oil, grapeseed oil, sunflower oil, soybean oil etc.; mineral oils such as petroleum jelly, paraffin, silicone, etc.; aliphatic or cyclic hydrocarbons or alternatively, for example, mecium-chain triglycerides (C8 to C12 in particular), absolute ethanol, isopropanol, methanol.

An emollient and/or spreading agent and/or film-forming agent will preferably be added, chosen in particular from:

polyvinylpyrrolidone, polyvinyl alcohols, copolymers of vinyl acetate and vinylpyrrolidone, polyethylene glycols, benzyl alcohol, mannitol, glycerol, sorbitol, polyoxyethylenated sorbitan esters, lecithin, sodium carboxymethylcellulose, silicone oils such as a 45V2 oil, anionic surfactants such as alkaline stearates, in particular sodium, potassium or ammonium stearate; calcium stearate, triethanolamine stearate; sodium abietate; alkyl sulphates, in particular sodium lauryl sulphate and sodium cetyl sulphate; sodium dodecylbenzene sulphonate; sodium dioctyl sulphosuccinate; fatty acids, in particular those derived from coconut oil, cationic surfactants such as water-soluble quaternary ammonium salts of formula $N^+R'R''R'''R''''$, $Y^-$ in which the radicals R are optionally hydroxylated hydrocarbon radicals, and $Y^-$ is an anion of a strong acid such as halide, sulphate and sulphonate anions; cetyltrimethylammonium bromide is among the cationic surfactants which may be used, amine salts of formula $N^+R'R''R'''$ in which the radicals R are optionally hydroxylated hydrocarbon radicals; octadecylamine hydrochloride is among the cationic surfactants which may be used, nonionic surfactants such as optionally polyoxyethylenated sorbitan esters, in particular Polysorbate 80, polyoxyethylenated alkyl ethers; polyoxypropylenated fatty alcohols such as polyoxypropylene-15 stearyl ether; polyethylene glycol stearate, polyoxyethylenated derivatives of castor oil, polyglycerol esters, polyoxyethylenated fatty alcohols, polyoxyethylenated fatty acids, copolymers of ethylene oxide and propylene oxide, amphoteric surfactants such as lauryl-substituted betaine compounds;

or a mixture of at least two of these.

The solvent will be used as a proportion of the concentration of compound I and of its solubility in this solvent.

For example, the compound of formula I has a solubility of 4.3% w/V in acetyl tributyl citrate. It will be sought to have the lowest possible volume.

The vehicle makes up the difference to 100%.

The emollient is preferably used in a proportion of 0.1 to 10%, in particular from 0.25 to 5% by volume.

Instead of a pour-on solution, the compositions according to the invention may also, but considerably less preferably, be prepared in the form of a bath into which the animal is immersed or alternatively in the form of a solution to be sprayed onto the animal's body.

For a curative composition intended to be applied externally onto a myiasis wound which is already established, it is preferred that the composition according to the invention be in the form of a solution to be sprayed.

The dose to be delivered onto the wound is between 0.01 and 100 mg of compound of formula I as defined above. It is more preferably between 0.1 and 50 mg.

In a particularly advantageous manner, the dose is between 5 and 15 mg, to be applied once or twice onto the wound. The composition may thus be prepared in the form of a composition to be sprayed or in the form of a liquid aerosol, or alternatively in the form of a powder for spraying or administration in the form of a solid aerosol, or alternatively pastes or solution to be spread on.

For a spray formulation, it may be envisaged to combine the compound according to formula I with an alcoholic vehicle.

The composition for this local treatment may also advantageously comprise gentian violet or another antiseptic with a dye or alternatively an antibiotic with a dye.

It is particularly remarkable to note that by virtue of the composition according to the invention, wounds, even very large wounds, are treated with surprising efficacy and the efficacy after treatment does not even need to be checked; the animal may be released immediately.

The dose is preferably contained in a volume of 3 to 6 ml to be sprayed on.

The invention also relates to compositions which may be administered via a route allowing good systemic distribution, preferably, which may be administered only once or a small number of times for a duration of activity of at least one month and which may advantageously be two or three months, or even six months.

The dose may be administered in particular via the oral or parenteral route or by means of a topical formulation with transcutaneous action. The dose of compounds of formula I defined above is preferably between 0.01 and 100 mg and preferably 1 to 50 mg/kg of body weight of the animal and especially from 1 to 10 mg/kg.

The composition may optionally be prepared at the time of use, for example by simple mixing of a preparation as powder or preferably as a solution of a compound of formula (I), into the animal's food.

The composition may, however, also be provided in any other form which is suitable for oral administration, such as, for example, drinkable solution or suspension, emulsion, microemulsion, cream, pellet, tablet, gelatin capsule or the like.

However, it is particularly preferred for the composition to allow controlled release into the rumen and thus a preparation in the form of a gradual-release intraruminal bolus or other rumen-resistant formulation will be clearly preferred.

The composition may also be prepared for parenteral, preferably subcutaneous or intramuscular, administration, the compound of formula (I) then being contained in a biologically suitable liquid excipient for injection, in the form of a solution, suspension, emulsion or microemulsion.

The composition may be prepared especially in particulate form, in particular nanoparticles and nanocapsules, microparticles, microcapsules or liposomes, or alternatively in the form of an implant.

It is moreover understood that the compositions according to the invention may also contain, if necessary, one or more other parasiticides.

The subject of the invention is also the use of the compounds of formula I, as defined above, for the preparation of compositions for controlling myiasis in cattle and sheep, as described above.

Other advantages and characteristics of the invention will become apparent on reading the description, given by way of non-limiting example, which follows.

EXAMPLE 1

Preparation of a Pour-on Solution for Cattle:

| Ingredient | Function | Amount |
| --- | --- | --- |
| Fipronil | active substance | 1 g |
| Polyoxypropylene-15 stearyl ether | emollient | 5 g |
| Acetyl tributyl citrate | solvent | 30 g |

-continued

| Ingredient  | Function | Amount    |
|-------------|----------|-----------|
| Soybean oil | diluent  | qs 100 ml |

The Fipronil is dissolved in the solvent before being mixed with the other ingredients. A 1% Fipronil solution is thus obtained.

EXAMPLE 2

Protection of Cattle Against *Dermatobia hominis*:

The following two tests were carried out on cattle about 2 years old in two endemic zones. In each test, a group of 30 animals and a control group also of 30 animals were tested. The dose poured onto the animal was 1 ml per 10 kg of the composition of Example 1.

The animals were subjected to natural infestation in the open air. The live nodules were counted on each animal every week or every two weeks.

|         | 1st Test |     |      |     |     |     |     |
|---------|----------|-----|------|-----|-----|-----|-----|
| Weeks   | 0 (D0)   | 1   | 2    | 4   | 6   | 8   | 10  |
| Control group | 7*   | 8*  | 7*   | 10* | 10* | 10* | 8*  |
| Treated group | 12*  | 93% | 100% | 99% | 98% | 92% | 75% |

*Average number of live nodules per animal
% Percentage of efficacy

It is seen that this composition had an excellent curative activity in the two weeks following the treatment, as well as very good residual activity for at least six weeks.

By comparison, treatments using organophosphorus (Neguvon) revealed an immediate actual curative activity but a rapid fall in residual activity.

|               | 2nd test |      |       |       |     |
|---------------|----------|------|-------|-------|-----|
| Weeks         | 1        | 2    | 4     | 6     | 8   |
| Control group | 50*      | 50*  | 56*   | 63*   | 40* |
| Treated group | 99%      | 100% | 98.7% | 91.9% | 35% |

This second test confirmed the efficacy demonstrated in the first test.

EXAMPLE 3

Test of Protection Against *Cochliomya hominivorax*:

A test was carried out in an endemic zone on two groups of 70 male head of cattle of about 18 months old, one of the groups being treated and the other serving as a control. Immediately after castration, the animals of the treated group received a dose of 1 ml per 10 kg of body weight of pour-on solution according to Example 1, the other group being untreated.

The animals were examined every 1 or 2 days for 2 weeks in order to search for signs of infestation by *C. hominivorax*, the main criterion being the presence of larvae for 4 consecutive days.

At ten days after the treatment, 59 of the untreated animals were infested with larvae for 4 days, whereas only two of the animals from the treated group were infested. The efficacy of Fipronil could be evaluated as being 96.6%.

This effect is obtained despite the presence of eggs on the animals, showing that the treatment was effective at the larval stage.

EXAMPLE 4

Preparation of an Injectable Composition:

A Fipronil solution at a concentration of 3.3% by weight per unit volume in a mixture of organic solvent and plant oil is mixed for subcutaneous administration.

EXAMPLE 5

Preparation of a Controlled-release Composition for Parenteral Administration:

Microspheres of polylactic, polylactic-glycolic acid PLA 100 D.L. with a molecular weight of about 100,000 are prepared at a concentration of 15% by weight per unit volume in water or in a plant oil or in a medium-chain triglyceride, with a content of 3.3% by weight per unit volume of Fipronil.

I claim:

1. A process for controlling myiasis including larvae of Calliphoridae, Oestridae, *Dermatobia hominis, Hypoderma bovis, Hypoderma lineatum, Cochliomya hominivorax, Cochliomya macellaria* or a combination thereof in an animal selected from the group consisting of cattle and sheep, which comprises administering to the animal via a route which results in systemic distribution, in a pharmaceutically-acceptable vehicle for such administration, an effective larvicidal amount of the compound 1-[2,6-Cl$_2$4-CF$_3$phenyl] 3-CN4-[SO—CF$_3$] 5-NH$_2$ pyrazole, whose common name is Fipronil.

2. A process for controlling myiasis in an animal selected from the group consisting of cattle and sheep, which comprises dermally administering in a pharmaceutically-acceptable vehicle for such administration an effective larvicidal amount, comprising a dose between 0.01 and 100 mg/kg, of the compound 1-[2,6-Cl$_2$4-CF$_3$phenyl] 3-CN4-[SO—CF$_3$] 5-NH$_2$ pyrazole, whose common name is Fipronil.

3. The process according to claim 2, wherein the dose is between 0.25 and 2.5 mg/kg, or 1 mg/kg.

4. The process according to claim 2, wherein the administering is of the compound in the form of a solution, suspension or emulsion including such a solution, suspension or emulsion which is administered by pouring onto the animal's back, or a pour-on composition.

5. The process according to claim 4, wherein the dose is in a vehicle in a volume of between 5 ml and 150 ml, and the animal is cattle.

6. The process according to claim 4, wherein the dose is in a vehicle in a volume of between 10 ml and 5 l, and the animal is sheep.

7. The process according to claim 4, wherein the compound is present in a concentration, by weight per unit volume, of between 0.1 and 10%.

8. The process according to claim 2, wherein the compound is administered with an antiseptic with a dye or alternatively an antibiotic with a dye.

9. The process according to claim 2, wherein the compound is present in a volume of from 3 to 6 ml of vehicle in a spray form.

10. The process according to claim 1, wherein the larvae are from at least one of: Oestridae, *Dermatobia hominis, Hypoderma bovis, Hypoderma lineatum*, Calliphoridae, *Cochliomyia hominivorax* and *Cochliomyia macellaria*.

11. The according to claim 1, wherein the larvae are from at least one of: Calliphoridae, comprising Luciliae, including *Lucilia cuprina* and *Lucilia sericata*, and Oestridae, including *Oestrus ovis*.

12. A process for controlling myiasis in an animal selected from the group consisting of cattle and sheep, which comprises cutaneously administering to the animal, in a pharmaceutically-acceptable vehicle for such administration, an effective larvicidal amount of the compound 1-[2,6-Cl$_2$4-CF$_3$ phenyl] 3-CN 4-[SO—CF$_3$] 5-NH$_2$ pyrazole whose common name is Fipronil.

13. The process according to claim 12, wherein the cutaneous administering is by a pour-on solution.

14. A process for controlling and treating myiasis in an animal selected from the group consisting of cattle and sheep, which comprises externally administering to the animal into or onto a myiasis wound, in a pharmaceutically-acceptable vehicle for such administration, an effective larvicidal amount of the compound 1-[2,6-Cl$_2$ 4-CF$_3$ phenyl] 3-CN 4-[SO—CF$_3$]5-NH$_2$ pyrazole, whose common name is Fipronil.

15. The process according to claim 14, wherein the administering is of the compound in the form of a spray solution, a liquid aerosol, a spray powder, a solid aerosol, or a spread on paste.

16. A process for controlling myiasis in an animal selected from the group consisting of cattle and sheep, which comprises orally administering to the animal, in a pharmaceutically-acceptable vehicle for such administration, an effective larvicidal amount of the compound 1-[2,6-Cl$_2$ 4-CF$_3$ phenyl] 3-CN 4-[SO—CF$_3$] 5-NH$_2$ pyrazole, whose common name is Fipronil.

17. The process of claim 16 wherein the compound is orally administered in a form selected from the group consisting of a drinkable solution, suspension, emulsion, microemulsion, a cream, a pellet, a tablet, a gelatin capsule, and a gradual-release intraruninal bolus or other rumen-resistant formulation.

18. A process for controlling myiasis in an animal selected from the group consisting of cattle and sheep, which comprises parenterally administering to the animal, in a pharmaceutically-acceptable vehicle for such administration, an effective larvicidal amount of the compound 1-[2,6-Cl$_2$ 4-CF$_3$ phenyl] 3-CN 4-[SO—CF$_3$] 5-NH$_2$ pyrazole, whose common name is Fipronil.

19. A process for controlling myiasis in an animal selected from the group consisting of cattle and sheep, which comprises administering to the animal, at a frequency selected from the group consisting of less than monthly, annually, and at most monthly during myiasis season, via a route which results in systemic distribution, in a pharmaceutically-acceptable vehicle for such administration, an effective larvicidal amount of the compound 1-[2,6-Cl$_2$ 4-CF$_3$ phenyl] 3-CN 4-[SO—CF$_3$] 5-NH$_2$ pyrazole, whose common name is Fipronil.

20. The process of claim 14 wherein the administering is of between 0.01 and 100 mg of the compound of formula (I).

21. The process according to claim 20 wherein the administering is once or twice of between 5 and 10 mg of the compound of formula (I).

22. The process of claim 14 wherein the administering is of the formula (I) compound in a vehicle comprising a antiseptic with a dye or an antibiotic with a dye.

23. The process of claim 14 wherein the administering is spraying of from 3 to 6 ml of a composition containing the formula (I) compound and a vehicle.

24. The process of claim 18 wherein the compound is parenterally administered in a form selected from the group consisting of a solution, suspension, emulsion and microemulsion and including a biologically-acceptable liquid excipient for injection.

25. The process according to claim 24 wherein the compound is in particulate form selected from the group consisting of nanoparticles, nanocapsules, microparticles, microcapsules and liposomes.

26. The process according to claim 25, wherein the compound is administered in an amount of between 0.01 and 100 mg.

27. A process for controlling myiasis in an animal selected from the group consisting of cattle and sheep comprising administering an effective larvicidal dose of the compound 1-[2,6-Cl$_2$ 4-CF$_3$ phenyl] 3-CN 4-[SO—CF$_3$] 5-NH$_2$pyrazole, whose common name is Fipronil.

28. A process for controlling myiasis in an animal selected from the group consisting of cattle and sheep, which comprises administering to the animal via a route which results in systemic distribution, in a pharmaceutically-acceptable vehicle for such administration, an effective larvicidal amount of the compound 1-[2,6-Cl$_2$ 4-CF$_3$ phenyl] 3-CN 4-[SO—CF$_3$] 5-NH$_2$ pyrazole, whose common name is Fipronil.

29. A process for controlling myiasis in an animal selected from the group consisting of cattle and sheep, which comprises administering to the animal an effective larvicidal amount of the compound 1-[2,6-Cl$_2$ 4-CF$_3$ phenyl] 3-CN 4-[SO—CF$_3$] 5-NH$_2$ pyrazole, whose common name is Fipronil in a pour-on formulation comprising a solution, suspension or emulsion.

30. The process according to claim 27 wherein the compound is administered in a vehicle in an amount between 0.01 and 100 mg/kg or between 0.1 and 10 mg/kg.

31. The process according to claim 30 wherein the compound is administered in an amount between 0.25 and 2.5 mg/kg, or 1 mg/kg.

32. The process according to claim 31, wherein the compound is administered in the form of a solution, suspension or emulsion pour-on composition.

33. The process according to claim 32, wherein the compound is administered in a vehicle with a volume of between 5 ml and 150 ml and the animal is cattle.

34. The process according to claim 32, wherein the compound is administered in a volume of between 10 ml and 5 l and the animal is sheep.

35. The process according to claim 32, wherein the compound is administered in a concentration by weight per unit volume between 0.1 and 10%.

36. The process according to claim 27, wherein the compound is administered in the form of a solution to be sprayed, or in the form of a liquid aerosol, or in the form of a powder for spraying, or in the form of a solid aerosol, or in the form of a paste or solution to be spread on.

37. The process according to claim 36, wherein the compound is administered in a dose between 5 and 15 mg and the administering is once or twice onto or into a myiasis wound.

38. The process according to claim 27, wherein the administering comprises administering the compound in the form of a pour-on solution.

39. The process according to claim 27, wherein the administering comprises administering the compound externally onto a myiasis wound.

40. The process according to claim 27, wherein the compound of formula (I) is administered with an antiseptic with a dye or antibiotic with a dye.

41. The process of claim 40 wherein the antiseptic with a dye comprises gentian violet.

42. The process of claim 27 wherein the cattle and sheep are open-pasture reared.

43. The process of claim 2 wherein the cattle and sheep are open-pasture reared.

44. The process of claim 42 wherein the administering is dermal or cutaneous of between 0.01 and 100 mg/kg of the formula (I) compound.

45. The process of claim 42 wherein the administering is dermal or cutaneous of between 0.25 and 2.5 mg/kg.

46. The process of claim 45 wherein the administering is of a pour-on composition comprising the formula (I) compound.

47. The process of claim 46 wherein the composition comprises a vehicle present in a volume of between 5 ml and 150 ml.

48. The process of claim 46 wherein the formula (I) compound is present in an amount, by weight per unit volume, of between 0.1 and 10%.

49. The process of claim 43 wherein the administering is annually.

50. The process of claim 43 wherein the administering of at most monthly during myiasis season.

51. The process of any one of claims 1, 28, 29, 12, 14, 16, 18, 19, 17 or 24 wherein the cattle and sheep are open-pasture reared.

52. A method for raising livestock comprising cattle or sheep, said method comprising open pasture rearing of the livestock and controlling, preventing, or treating myiasis in the cattle or sheep comprising administering an effective larvicidal dose of the compound 1-[2,6-$Cl_2$ 4-$CF_3$ phenyl] 3-CN 4-[SO—$CF_3$] 5-$NH_2$ pyrazole, whose common name is Fipronil.

53. The method of claim 52 wherein the administering of the compound is at a frequency selected from the group consisting of less than monthly, annually, and at most monthly during myiasis season.

* * * * *